US00PP20292P2

(12) United States Plant Patent
Cain

(10) Patent No.: US PP20,292 P2
(45) Date of Patent: Sep. 15, 2009

(54) GRAPEVINE 'IFG 31-077'

(50) Latin Name: *Vitis vinifera*
Varietal Denomination: IFG 31-077

(75) Inventor: David W. Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 0 days.

(21) Appl. No.: 12/215,931

(22) Filed: Jun. 27, 2008

(51) Int. Cl.
*A01H 5/00* (2006.01)

(52) U.S. Cl. ..... Plt./205

(58) Field of Classification Search ..... Plt./205
See application file for complete search history.

*Primary Examiner*—Annette H Para
(74) *Attorney, Agent, or Firm*—Townsend and Townsend and Crew LLP

(57) ABSTRACT

This invention is a new and distinctive grapevine 'IFG 31-077'. 'IFG 31-077' produces large, elongated, fully black, naturally large seedless fruits that ripen early and possess high sugar content and superior eating quality. The clusters have strong stems with good berry attachment.

1 Drawing Sheet

Latin name of the genus and species of the plant claimed: *Vitis vinifera.*

Variety denomination: 'IFG 31-077'.

BACKGROUND OF THE INVENTION

The new and distinct grapevine described and claimed herein originated from a hand pollinated cross of the Summer Royal variety (non-patented) and the Regal variety (South African PBR ZA971795)) hybridized in May 2001. The abortive seed traces were subsequently embryo cultured and the resulting population of plants were planted in the field in April 2002. The present variety of grapevine was selected as a single plant from within a population of 106 plants in July 2003 and was first asexually propagated by hardwood cuttings in December 2003. The resulting propagules were planted during April 2004 near Delano, Kern County, Calif. and were found to reproduce true-to-type through at least three generations of asexual reproduction.

BRIEF SUMMARY OF THE INVENTION

'IFG 31-077' was selected on the basis of a unique grouping of characteristics, including the ability to produce large, elongated, fully black, naturally large seedless fruits that ripen early and possess high sugar content and superior eating quality. The clusters have strong stems with good berry attachment.

To the inventor's knowledge, the known varieties to which the new grapevine variety is most similar are the parent varieties, the Sugrathirteen variety (U.S. Plant Pat. No. 10,434), and the Mariah variety (U.S. Plant Pat. No. 9,040). 'IFG 31-077' can be distinguished from these varieties based on the unique combination of characteristics for which it was selected. 'IFG 31-077' can further be distinguished from these known varieties as follows.

'IFG 31-077' can be distinguished from its parent the Summer Royal (non-patented) variety by having much more elongated berries as opposed to the nearly round berries of Summer Royal. The new variety ripens 7 days or more before the Summer Royal variety. The vine of the new variety is more vigorous and robust than the vine of the Summer Royal variety.

'IFG 31-077' differs from its parent the Regal variety by possessing black rather than white fruits. Berries of the new variety are slightly less elongated than the Regal variety. Berries of the new variety more readily attain high sugar content and are of superior eating quality as compared to the Regal variety.

'IFG 31-077' most closely resembles the Sugrathirteen variety in having somewhat similar color, fruit shape and an early ripening period. The new variety differs from the Sugrathirteen variety by having darker more fully black fruits that will attain full color even under low light conditions thus requiring less manipulation of the canopy to obtain commercially acceptable color. The new variety possesses slightly smaller berry size and berries are slightly softer and juicier. The new variety more readily attains high sugar content and has somewhat more acid giving a better sugar acid balance.

'IFG 31-077' somewhat resembles the Mariah variety however it differs from the Mariah variety by having a larger average berry size (6.1 g vs. 4.8 g). The new variety can further be distinguished from the Mariah variety by having more elongated and narrower berry as opposed to the shorter more nearly round berries of the Mariah variety. The new variety is responsive to gibberellic acid application to reduce berry number and increase berry size and does not show phytotoxicity to normal levels of gibberellic acid.

BRIEF DESCRIPTION OF THE DRAWINGS

The accompanying photographic illustration in FIG. 1 illustrates in full color 'IFG 31-077'. The photograph was taken using conventional techniques. The colors are as nearly true as is reasonably possible in a color representation of this type.

DETAILED DESCRIPTION OF THE INVENTION

Figure 1:
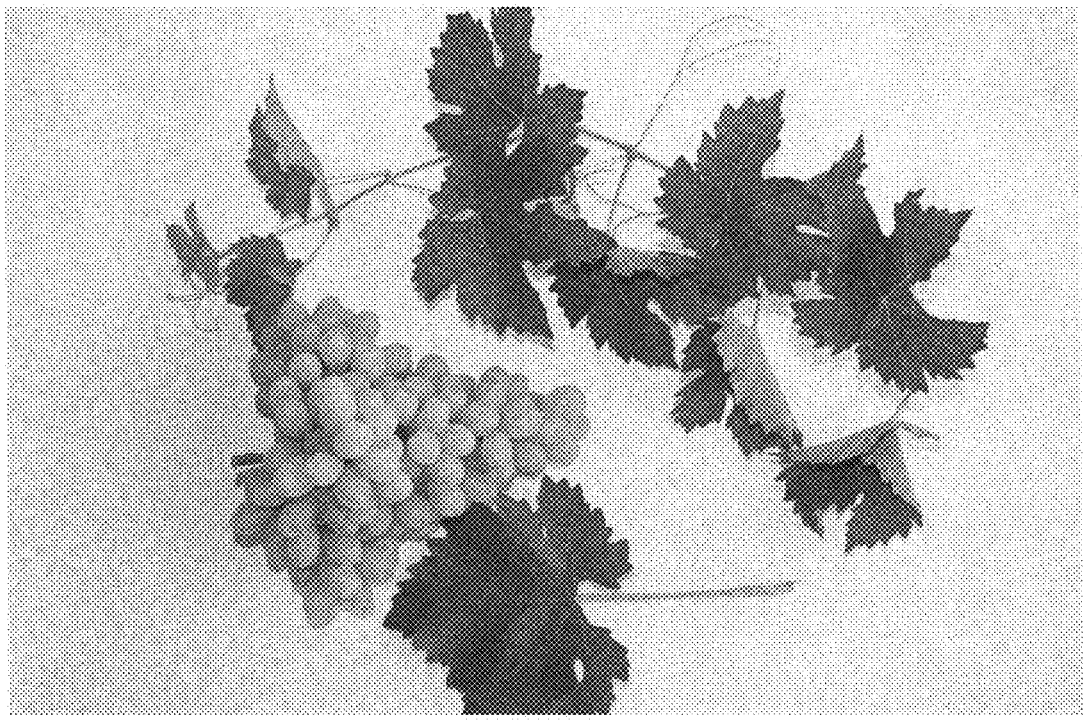
Figure 1:
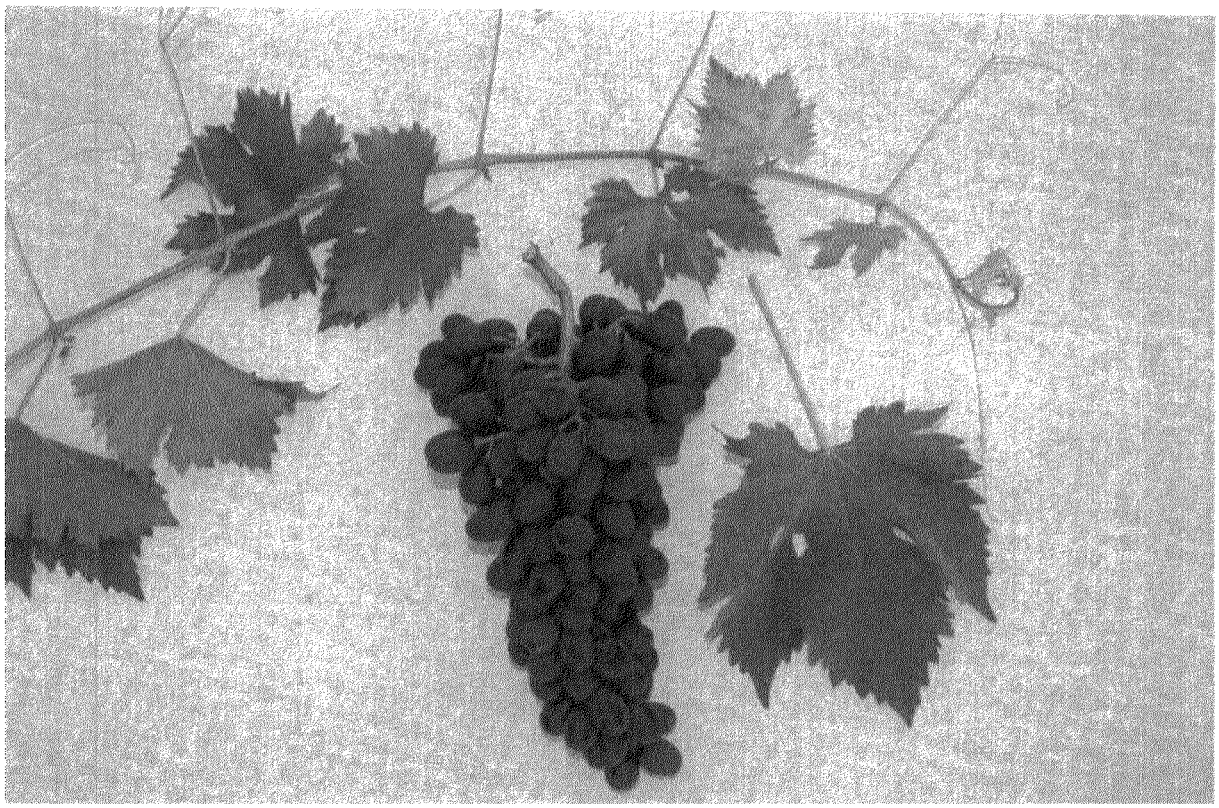

Throughout this specification, color names beginning with a small letter signify that the name of that color, as used in common speech, is aptly descriptive. Color names beginning with a capital letter designate values based upon R.H.S. Colour Chart, published by The Royal Horitcultural Society, London, England.

Throughout this specification subjective description values conform to those set forth by the International Plant Genetic Resources Institute publication 'Descriptors for Grape' (*Vitis* spp.) (1983) which was developed in collaboration with the Office International de la Vigne et du Vin (OIV) and the International Union for the Protection of New Varieties of Plants (UPOV).

The following descriptive matter pertains to 'IFG 31-077' plants grown in the vicinity of Delano, Kern County, Calif. during 2007–2008, and is believed to apply to plants of the variety grown under similar conditions of soil and climate elsewhere.

VINE

General:
- *Size.*—Very Large.
- *Vigor.*—Vigorous.
- *Density of foliage.*—Dense.
- *Productivity.*—Medium productive.
- *Root stock.*—Own root.
- *Training method.*—Typically spur pruned leaving two bud spurs.

Trunk:
- *Trunk diameter of* 4-*year-old vines at* 30 *cm above the soil line.*—7.4 cm.
- *Shape.*—Stocky.
- *Straps.*—Very long Split.
- *Surface texture.*—Medium.
- *Inner bark color.*—Greyed-Orange 174A.

SHOOTS

Young shoot:
- *Form of tip.*—Wide open.
- *Distribution of anthocyanin coloration of tip.*—Absent.
- *Intensity of anthocyanin coloration of tip.*—Absent.
- *Density of prostrate hairs of tip.*—Sparse.
- *Density of erect hairs of tip.*—Absent.
- *Color.*—Yellow Green 144A.

Woody shoot (mature canes):
- *Shape.*—Stocky.
- *Internode length.*—Long; About 13.7 cm.
- *Width at node.*—About 1.9 cm.
- *Cross section.*—Circular.
- *Surface.*—Striate.
- *Main color.*—Greyed-Orange about 166B to 166C.
- *Density of erect hairs of nodes.*—None.
- *Density of erect hairs on internodes.*—None.
- *Growth of axillary shoots.*—Strong, Approximately 23.2 cm.

Flowering shoot:
- *Vigor during flowering.*—Very strong.
- *Attitude during flowering on shoots not tied.*—Drooping.
- *Color.*—Dorsal side of internodes — Green with red stripes.
- *Color.*—Ventral side of internodes — Yellow Green 144A.
- *Color.*—Dorsal side of nodes — Yellow Green 144A.
- *Color.*—Ventral side of node — Yellow Green 144A.
- *Density of prostrate hairs of nodes.*—None to Very sparse.
- *Density of erect hairs on nodes.*—None.
- *Density of prostrate hairs on internode.*—None to Very sparse.
- *Density of erect hairs on internode.*—None.
- *Anthocyanin coloration of buds.*—Absent.

Tendrils:
- *Distribution on the shoot* (*at full flowering*)—Discontinuous.
- *Length of tendril.*—Long; About 29.2 cm.
- *Thickness.*—Medium.
- *Color.*—Yellow Green 144A.
- *Form.*—Bifurcated.
- *Number of consecutive tendrils.*—2.

LEAVES

Young leaves:
- *Color of upper surface of first four distal unfolded leaves.*—Copper yellow.
- *Average intensity of anthocyanin coloration of six distal leaves prior to flowering.*—Weak.
- *Density of prostrate hairs between veins* (*lower surface*).—Absent.
- *Density of prostrate hairs on veins.*—Very sparse.
- *Density of erect hairs between veins* (*lower surface*).—Absent.
- *Density of erect hairs on veins.*—Very sparse.

Mature leaves:
- *Average length.*—About 17.2 cm.
- *Average width.*—About 24.4 cm.
- *Mature leaf size.*—Very large.
- *Shape of blade.*—Circular.
- *Number of lobes.*—5.
- *Anthocyanin coloration of main veins on upper side of blade.*—Weak.
- *Mature leaf profile.*—Involute.
- *Blistering surface of blade upper surface.*—Strong.
- *Leaf blade tip.*—In the plane of the leaf.
- *Undulation of margin.*—Pronounced.
- *Thickness.*—Medium.
- *Undulation of blade between main and lateral veins.*—Overall.
- *Shape of teeth.*—Both sides convex.
- *Length of teeth.*—Medium.
- *Ratio length/width of teeth.*—Small.
- *Shape of upper lateral sinuses.*—Slightly overlapping.
- *Depth of upper lateral sinuses.*—Shallow.
- *General shape petiole sinus.*—Lobes strongly overlapping.
- *Shape of base of upper leaf sinuses.*—V-shaped.
- *Density of prostrate hairs between veins on lower surface of blade.*—None or very sparse.
- *Density of erect hairs between veins on lower surface of blade.*—None.
- *Density of prostrate hairs on main veins on lower surface of blade.*—Very sparse.
- *Density of erect hairs on main veins on lower surface of blade.*—Sparse.
- *Density of prostrate hairs on main veins on upper surface of blade.*—None or very sparse.
- *Density of erect hairs on main veins on upper surface of blade.*—None or very sparse.

*General shape petiole sinus.*—Lobes very strongly overlapping.
*Shape of base of petiole sinus.*—V-shaped.
*Mature leaf tooth at petiole sinus.*—Absent.

Upper surface:
*Color.*—Green 139A.
*Anthocyanin coloration of main veins.*—Absent.
*Surface appearance.*—Semi-glossy to dull.
*Blistering surface of blade.*—Weak to medium.

Lower surface:
*Color.*—Green 138A.
*Anthocyanin coloration of main veins (lower surface).*—Absent.
*Surface texture.*—Rugose.
*Surface appearance.*—Semi-glossy.

Petiole:
*Length.*—About 11.4 cm.
*Length of petiole compared to middle vein.*—Slighty shorter.
*Density of prostrate hairs on petiole.*—None.
*Density of erect hairs on petiole.*—None.

Buds:
*Bud fruitfulness.*—Basal: Mostly fruitful.
*Position of first fruitful shoot on previous season cane.*—1st–2nd node.
*Time of bud burst.*—Early, Feb. 29, 2008 (measurement from one location).

FLOWERS

General:
*Flower sex.*—Hermaphrodite.
*Length of first inflorescence.*—17.2 cm (at full bloom).
*Position of first flowering and fruiting node.*—5th node (current season growth).
*Number of inflorescence per flowering shoot.*—Up to 1.
*Time of bloom.*—Early–Medium as compared with similar varieties in the growing area of Delano, Calif.

FRUIT

General:
*Ripening period.*—Early; Approximately Jul. 17, 2007 (measurement from a single location).
*Use.*—Fresh market.
*Keeping quality.*—Good.
*Resistance to.*—Insects: Average typical of *Vitis vinifera* species. diseases: Average typical of *Vitis vinifera* species.
*Refractometer test.*—Solid-sugar: About 20.0 Brix.
*Brix/acid.*—About 45.8.
*Titratable acidity.*—About 0.44.
*Juice pH.*—About 3.45.

Cluster:
*Mature cluster length (peduncle excluded).*—About 23.5 cm.
*Mature cluster width.*—About 16.6 cm.
*Mature cluster weight.*—About 665 g.
*Bunch density.*—Medium to Dense.
*Number of berries.*—About 140.
*Form.*—Conical.

Peduncle:
*Length of peduncle.*—Approximately 5.0 cm.
*Lignification of peduncle.*—Weak.

Berry:
*Uniformity of size.*—Uniform.
*Single berry weight.*—About 6.1 g when treated with gibberellic acid.
*Shape.*—Elongated ovate.
*Seed.*—Rudimentary to small seed traces.
*Berry dimensions.*—Longitudinal axis: About 27.2 mm. horizontal axis: About 18.5 mm.
*Skin color (without bloom).*—Black. 202A.
*Berry firmness.*—Medium.
*Particular flavor.*—Neutral.
*Bloom (cuticular wax).*—Weak to Medium.
*Berry separation from pedicel.*—Medium.

Skin:
*Thickness.*—Medium.
*Texture.*—Medium.
*Reticulation.*—Absent.
*Tenacity.*—Tenacious to flesh.

What is claimed is:

1. A new and distinct variety of grapevine plant having the characteristics substantially as described and illustrated herein.

* * * * *

UNITED STATES PATENT AND TRADEMARK OFFICE

CERTIFICATE OF CORRECTION

PATENT NO. : PP 20,292 P2
APPLICATION NO. : 12/215931
DATED : September 15, 2009
INVENTOR(S) : David W. Cain It is certified that error appears in the above-identified patent and that said Letters Patent is hereby corrected as shown below:

Delete the Drawing Sheet consisting of FIG. 1 and substitute therefore the attached Drawing Sheet consisting of FIG. 1.

Signed and Sealed this

Twentieth Day of April, 2010

David J. Kappos

David J. Kappos
*Director of the United States Patent and Trademark Office*